United States Patent [19]

Czornyj et al.

[11] 4,169,904
[45] Oct. 2, 1979

[54] PREPARATION OF POLYMER MONOMOLECULAR FILMS

[75] Inventors: George Czornyj, Wappingers Falls, N.Y.; Jerome D. Swalen, Los Gatos, Calif.; Anthony W. Wu, Fishkill, N.Y.

[73] Assignee: International Business Machines Corporation, Armonk, N.Y.

[21] Appl. No.: 867,057

[22] Filed: Jan. 5, 1978

[51] Int. Cl.$^2$ .............................................. B05D 3/06
[52] U.S. Cl. ................................... 427/44; 204/159.20; 252/12; 252/33.6; 252/54.6; 252/58; 260/408; 427/54; 428/422
[58] Field of Search ............... 427/44, 54; 252/33.6, 252/12, 58, 54.6; 204/159.2; 428/422, 463, 426, 446, 447, 470; 260/408

[56] References Cited

U.S. PATENT DOCUMENTS

| | | | |
|---|---|---|---|
| 2,198,275 | 4/1940 | Reiff et al. | 252/33.6 X |
| 2,662,835 | 12/1953 | Reid | 428/422 |
| 2,680,717 | 6/1954 | Little, Jr. | 252/33.6 |
| 2,806,867 | 9/1957 | Barnhart et al. | 252/33.6 X |
| 3,575,940 | 4/1971 | Katsushima et al. | 428/422 X |
| 3,749,744 | 7/1973 | Siddall et al. | 260/408 X |
| 4,002,657 | 1/1977 | Jäger | 260/408 |
| 4,004,951 | 1/1977 | Dorsey, Jr. | 428/470 X |
| 4,052,321 | 10/1977 | Claiborne | 260/408 X |

OTHER PUBLICATIONS

Cemel et al., J. Polymer Science, A-1, vol. 10, pp. 2061–2083 (1972), J. Wiley & Son, Inc.

Primary Examiner—Michael F. Esposito
Assistant Examiner—Thurman K. Page
Attorney, Agent, or Firm—Joseph G. Walsh

[57] ABSTRACT

A substrate surface is lubricated or passivated by applying thereto a monomolecular layer of a compound having the formula

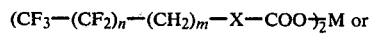

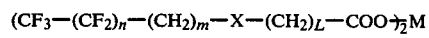

wherein n is 6 to 20, each of m and L is 6 to 10, X is —CH=CH— or —C≡C—, and M is a divalent cation, and polymerizing said layer in situ.

5 Claims, No Drawings

PREPARATION OF POLYMER MONOMOLECULAR FILMS

BACKGROUND OF THE INVENTION

The present invention deals with a method for lubricating and/or passivating a solid substrate surface. This end is achieved by applying to the surface a monomolecular layer of a metal salt of an unsaturated partially fluorinated fatty acid and polymerizing said layer in situ.

PRIOR ART

It is well known in the art to use fluorinated, particularly perfluorinated, materials as coatings for lubrication or for passivation. Fluorinated materials are noted for possession of low coefficients of friction, low surface energy and a high degree of chemical inertness. It remains, however, a difficult problem to adhere a perfluorinated material to a substrate. Perfluorinated long chain acids and salts are rigid and have a tendency to crystalize. They also have relatively high viscosity, high vapor pressure and low cohesive energy. The combination of these properties makes it very difficult to build up a stable monolayer assembly of such a material on a substrate.

The prior art shows that multi-layer or monomolecular layers of vinyl stearate can be polymerized by a solid state reaction. See Peterman et al, J. Colloid and Interface Sci., 47, 705 (1974), and A. Cemel et al, J. Polym. Sci., A-1, 2061 (1972).

SUMMARY OF THE INVENTION

According to the present invention, a solid substrate is covered with a cross-linked monomolecular layer of fluorinated material which imparts the properties of lubrication and passivation. The fluorinated material is a metal salt of an unsaturated partially fluorinated fatty acid which is polymerized as a monomolecular layer in situ upon the substrate.

The compounds useful in the present invention have the formula

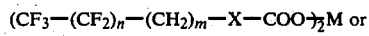

or

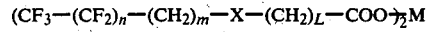

wherein n is 6 to 20, each of m and L is 6 to 10, X is —CH=CH— or —C≡C—, and M is a divalent cation. The calcium, barium and cadmium salts are particularly preferred. The active —CH=CH— or —C≡C— is strategically placed in the carbon-carbon backbone to promote film condensation and polymerization.

The particular solid substrates of greatest interest for the use of the present invention are hydrophilic surfaces like and oxidized metal, semi-conductor or dielectric. As particularly important examples, there may be mentioned silicon dioxide, aluminum oxide, fused silica and glass. The salt group enhances the attachment of the monolayer to the substrate and also its thermal stability as shown by thermal gravimetric analysis. In addition, the double or triple bond, which is strategically placed between the carboxylic acid group and the $CF_2$ groups, undergoes solid state polymerization when exposed to ultraviolet radiation or gamma rays. (FT-IR shows for example that the —C≡C— disappears upon UV irradiation in agreement with polymerization taking place.) The polymerization results in a highly oriented thin polymer film which is insoluble due to cross-linking via the —C≡C— bond and consists of high molecular weight species. This film is conformal and pin-hole free. In addition, it has a low surface energy (contact angle of 94.5° with $CH_2I_2$). ESCA shows that the correct ratio of $CF_3/CF_2$ and C/F exists in the film. This film possesses the following advantages:

a. The deposition and polymerization occurs at room temperature so that sensitive metallurgies are not subjected to thermal stresses.

b. The film thickness is molecularly engineered and controlled by the length of the extended chain monomer length.

c. The fluorocarbon groups are not subject to bacteria attack as are some fully hydrogenated fatty acids.

d. Also, by judiciously controlling the F/C ratio, the lateral cohesive energy between the molecules can be increased to improve upon the film's thermal stability.

e. Mechanical durability and thermal stability of a high molecular weight cross-linked polymer.

A long alkyl chain is required for the monomer used in the present invention. To compensate for the larger cross section diameter of the fluorocarbon segment, a long alkane chain is required to allow cross linking through the double or triple bond upon exposure to gamma rays or ultra violet radiation. This is a topotactic requirement for polymerization or cross-linking to occur. That is, the double or triple bond distance must be close enough to each other to form a sigma bond.

In one preferred variation of the present invention, a certain fraction of conventional unsaturated compounds, for example x-tridecenoic acid or alkenes, may be mixed in with the fluorinated monomer during monolayer formation in order to compensate for the larger cross-sectional diameter of the fluorinated group. The presence of such an unsaturated material contributes to the cross-linking.

The partially fluorinated materials of the present invention may be synthesized by the procedures outlined and described below.

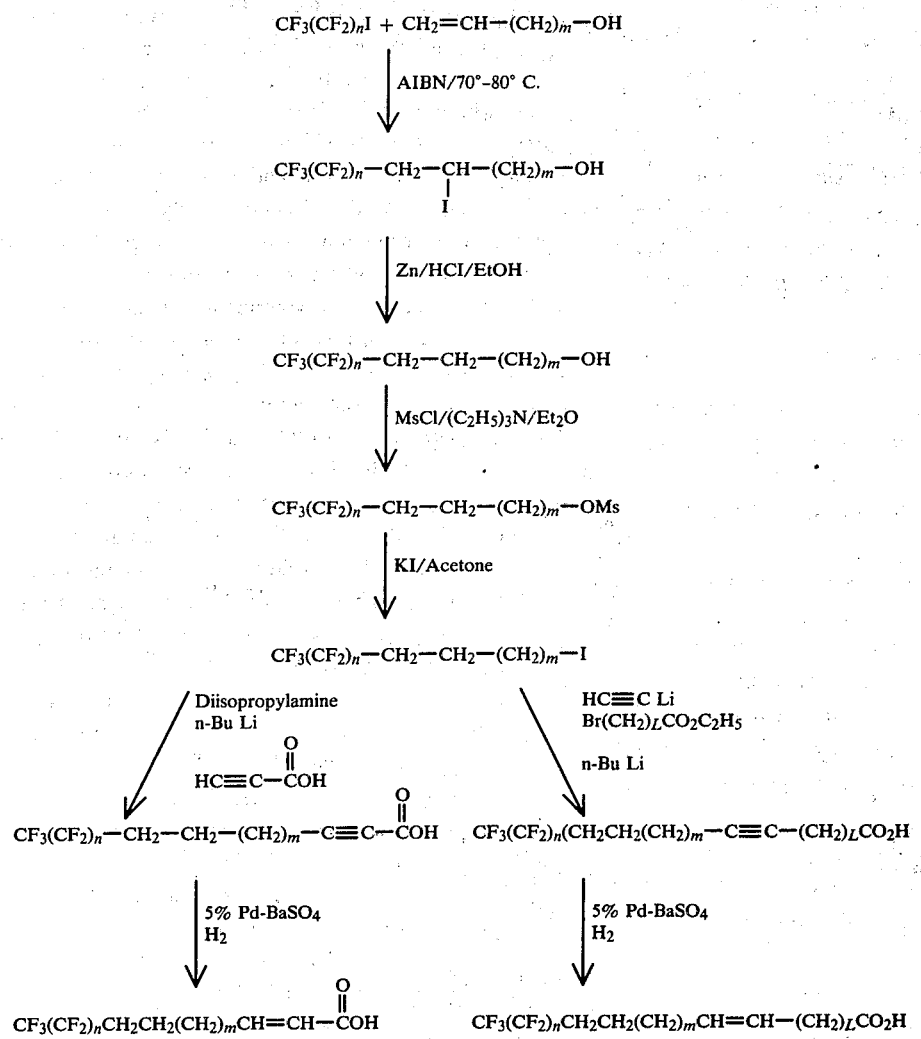

DESCRIPTION OF PREFERRED EMBODIMENTS

Addition of 1-Iodoperfluoroheptane to ω-undecylenyl alcohol using AIBN Initiator. ω-undecylenyl alcohol (17.1 g.; 0.10 mole), 1-iodoperfluoroheptane (49.6 g.; 0.10 mole), and azobisisobutyronitrile (AIBN) (1.64 g.; 0.01 mole) were heated under nitrogen at 70°–80° C. for 5 hr. and cooled to room temperature, whenupon the whole mixture was solidified. Yield of the addition product was over 90%.

Zinc reduction of 1-Iodoperfluoroheptane adduct to ω-undecylenyl alcohol—A solution of the addition product (0.10 mole) in 150 ml. ethyl alcohol was saturated with anhydrous hydrogen chloride and heated to 50°–60° C. Zinc powder (9.8 g.; 0.15 mole) was added periodically at such a rate that no excessive foaming should occur. The solution was resaturated with dry hydrogen chloride at times when zinc dust failed to react. After the addition of zinc had completed, the solution was continued to reflux for an hour. Alcohol was removed by distillation at reduced pressure and the residue was poured into water and extracted three times with ether. After drying over anhydrous magnesium sulfate, the solvent was removed under reduced pressure and the product, $CF_3(CF_2)_6(CH_2)_{11}OH$ was isolated in 75% yield.

Anal. Calcd. for $C_{18}H_{23}F_{15}O$: C, 40.00; H, 4.26; F, 47.69. Found: C, 40.18; H, 5.10; F, 47.50.

Reaction of $CF_3(CF_2)_6(CH_2)_{11}OH$ with methanesulfonyl chloride—To a solution of $CF_3(CF_2)_6(CH_2)_{11}OH$ (2.70 g.; 0.02 mole) in 50 ml. anhydrous diethyl ether was added 0.7 ml. of triethylamine and cooled to 0° C. Methanesulfonyl chloride (0.4 ml; 0.02 mole) was added dropwise. After stirring at 0° C. for 0.5 hr., the reaction mixture was brought up to room temperature. The amine hydrochloride salt was filtered off and the remaining ether solution was evaporated to dryness to give quantitative yield of $CF_3(CF_2)_6(CH_2)_{11}OMs$, m.p. 50° C.

Anal. Calcd. for $C_{18}H_{25}F_{15}O_3S$: C, 36.89; H, 4.05; F, 46.12. Found: C, 37.55; H, 4.12; F, 46.72.

Reaction of $CF_3(CF_2)_6(CH_2)_{11}OMs$ with Potassium Iodide—$CF_3(CF_2)_6(CH_2)_{11}OMs$ (6.68 g.; 0.01 mole) and potassium iodide (3.32 g.; 0.01 mole) in 200 ml. reagent acetone was heated to reflux for 2 hr., cooled to room temperature and the solid residue was removed by filtration. The remaining acetone solution was evaporated to dryness to give $CF_3(CF_2)_6(CH_2)_{11}I$ in 85% yield, m.p. 32° C.

Anal. Calcd. for $C_{18}H_{22}F_{15}I$: C, 32.23; H, 3.38; F, 43.84. Found: C, 32.00; H, 3.35; F, 43.89.

Preparation of

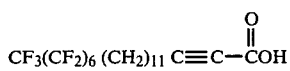

In a three-necked round bottom flask fitted with condenser, nitrogen inlet, drying tube, and septum were placed diisopropylamine (1.06 g. 0.01 mole), 21.0 ml. potassium dry tetrahydrofuran and 3.0 ml. of hexamethylphosphoramide. The reaction mixture was cooled to $-78°$ C. in a dry ice-acetone bath. n-Butyllithium (4.5 ml. of 2.5 M; 0.01 mole) was added dropwise with a syringe. After stirring at $-78°$ C. for an hour, a 10% solution of propiolic acid (0.35 g.; 0.0005 mole) in hexamethylphosphoramide (3.5 g.) was added dropwise while keeping the temperature below $-60°$ C. After stirring at $-78°$ C. for an hour $CF_3(CF_2)_6(CH_2)_{11}I$ (3.03 g.; 0.005 mole) in tetrahydrofuran (35 ml.) and hexamethylphosphoramide (5 ml.) was added dropwise. After an additional two hours, the reaction mixture was brought to room temperature, and let stir for 2 hours before being hydrolyzed with water. Acidified the solution with dilute HCl followed by extraction three times with diethyl ether. The combined ether extracts were dried over anhydrous magnesium sulfate.

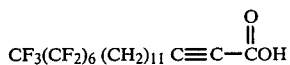

was isolated in 60% yield after all of the solvent had been removed under reduced pressure, m.p. 70° C.

Anal. Calcd. for $C_{21}H_{23}F_{15}O_2$: C, 42.57; H, 3.88; F, 48.14. Found: C, 4.50; H, 3.98; F. 48.10.

The monolayers were prepared from a $1 \times 10^{-3}$ molar solution in chloroform. Approximately 100 $\mu l$ of solution were placed on the water surface, drop by drop. The water was buffered to a pH from 5 to 7 and a temperature of 19° to 20° C. A weight of 70 mg (27 dynes/cm) pulled the float, compressing the monolayer coverage to an area of approximately $6.3 \times 30$ cm. Transfer to fused silica substrates was accomplished by dipping into and out of the tank.

Non-polymerized partially fluorinated fatty acid gave a contact angle of 94.5° with methylene iodide, showing a low energy surface. Cross linking was accomplished with a uv lamp and was monitored by the disappearance of the unsaturation.

These unsaturated polymerized partially fluorinated fatty acids convert a high energy surface to a low energy surface giving better lubricating properties.

What is claimed is:

1. A process for lubricating or passivating a solid substrate surface comprising applying thereto a monomolecular layer of material having the formula

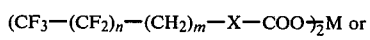

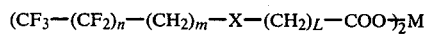

wherein n is 6 to 20, each of m and L is 6 to 10, X is $-CH=CH-$ or $-C\equiv C-$, and M is a divalent cation, and polymerizing said layer in situ by exposing it to radiation.

2. A process as claimed in claim 1 wherein the polymerization is carried out by exposing the monomolecular layer to ultra violet or gamma ray radiation.

3. A process as claimed in claim 1 wherein the solid substrate is a hydrophilic surface.

4. A process as claimed in claim 1 wherein the substrate is a metal oxide.

5. A process as claimed in claim 1 wherein the substrate is silicon dioxide.

* * * * *